United States Patent [19]
Dietz

[11] Patent Number: 5,485,850
[45] Date of Patent: Jan. 23, 1996

[54] MONITOR OF LOW PRESSURE INTERVALS WITH CONTROL CAPABILITIES

[76] Inventor: Henry G. Dietz, 80 Salisbury Ave., Garden City, N.Y. 11530

[21] Appl. No.: 106,083

[22] Filed: Aug. 13, 1993

[51] Int. Cl.⁶ ............................ A61B 5/08; A61M 16/00
[52] U.S. Cl. ................. 128/716; 128/204.23; 73/861.44
[58] Field of Search .................................. 128/716, 719, 128/722, 725, 724, 204.18, 204.23, 204.21, 205.24, 207.18, 726; 73/200.23, 861.44

[56] References Cited

U.S. PATENT DOCUMENTS

| | | | |
|---|---|---|---|
| 4,436,584 | 8/1982 | Boehringer | 128/719 |
| 4,986,269 | 1/1991 | Hakkinen | 128/204.23 |
| 5,024,219 | 6/1991 | Dietz | 128/204.21 |
| 5,052,400 | 10/1991 | Dietz | 128/722 |
| 5,117,819 | 6/1992 | Servidio et al. | 128/204.21 X |
| 5,134,995 | 8/1992 | Gruenke et al. | 128/204.23 |
| 5,303,699 | 4/1994 | Bonassa et al. | 128/204.21 |

FOREIGN PATENT DOCUMENTS 2188731  10/1987  United Kingdom ................... 128/722

*Primary Examiner*—Angela D. Sykes
*Assistant Examiner*—Samuel Gilbert

[57] ABSTRACT

A monitor that provides data obtained from the detection of very low positive, negative, or differential pressures, and can be used to control devices in health care and industry. An example of its use in health care is as a respiration monitor providing data that can be used to control devices associated with breathing while providing constant surveillance of the fundamental characteristics of air-breathing humans and animals. In industry it can act as a monitor that provides data by sensing very low pressures (negative, positive or differential) at intervals that can be used to detect positioning of low weight parts or act as a touch sensor for robotic equipment. Monitor detects pressure intervals by use of a vane type capacitance sensor capable of detecting pressures as low as 0.001 ounce per square inch. Monitor uses a micro-controller to control devices from data, obtained from sensor, by storing programs that govern, in predetermined manner, the operation of devices.

2 Claims, 8 Drawing Sheets

COMMON CATHOD

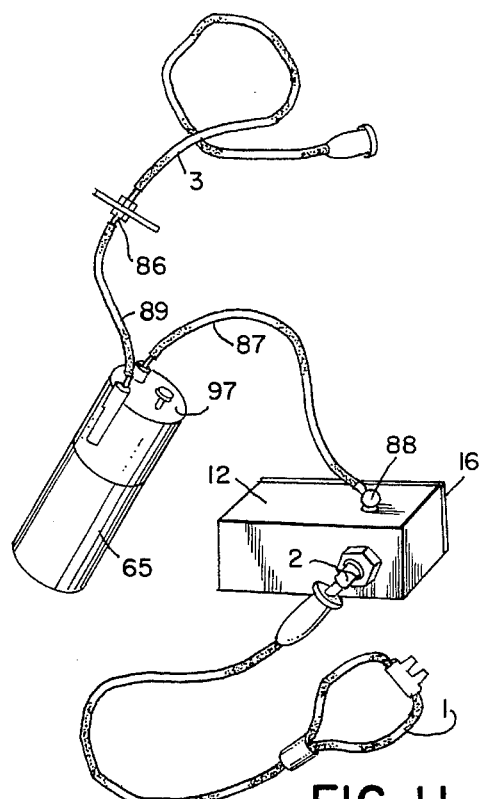
FIG. 11
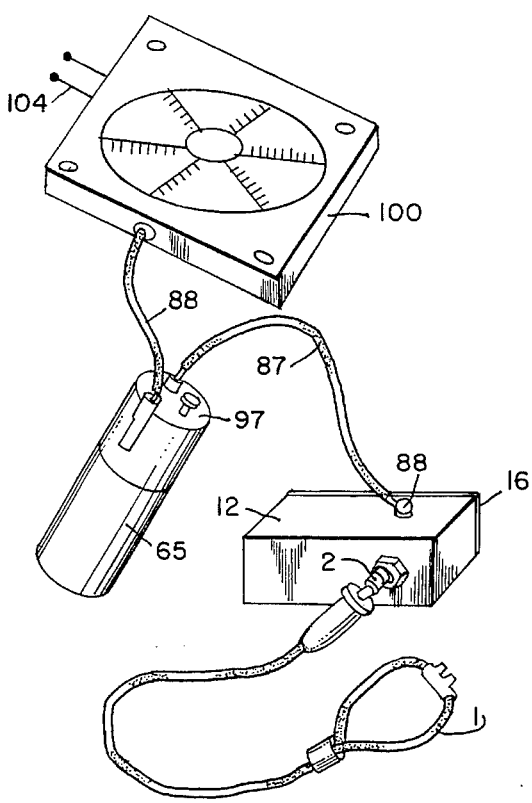
FIG. 12
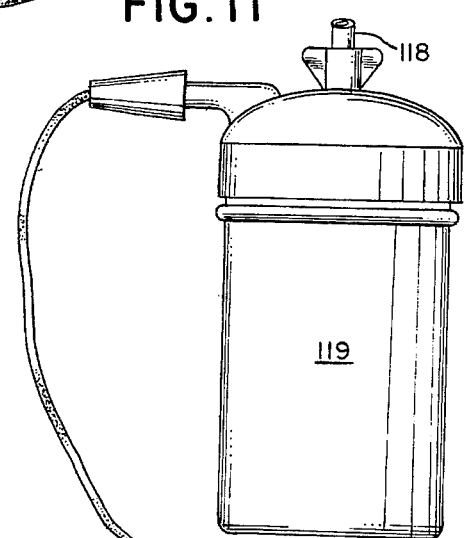
FIG. 13A
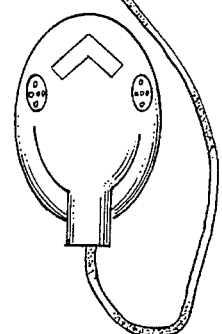

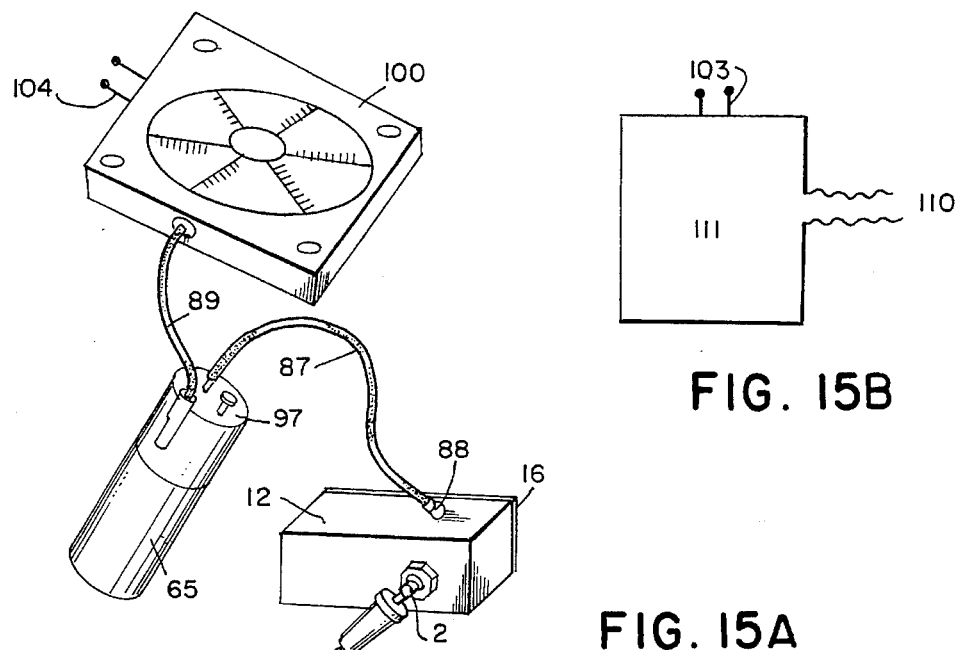
FIG. 15B
FIG. 15A
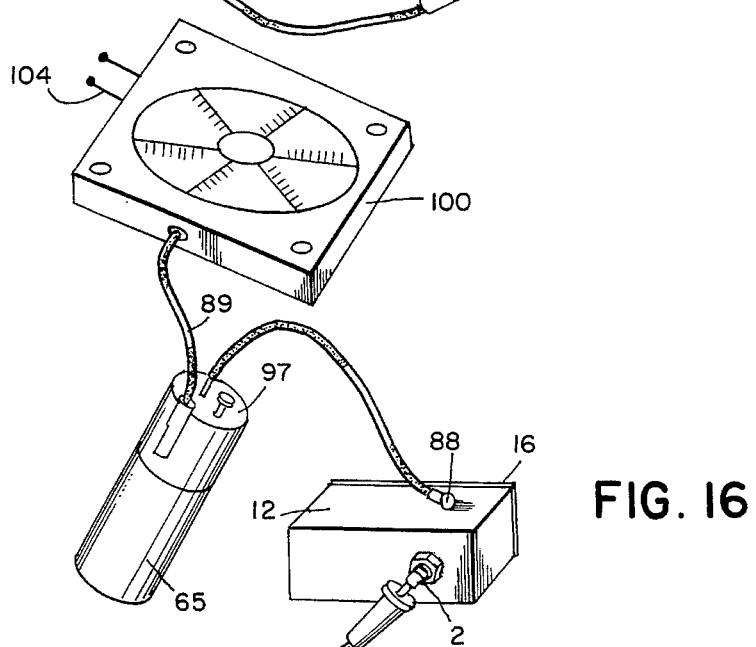
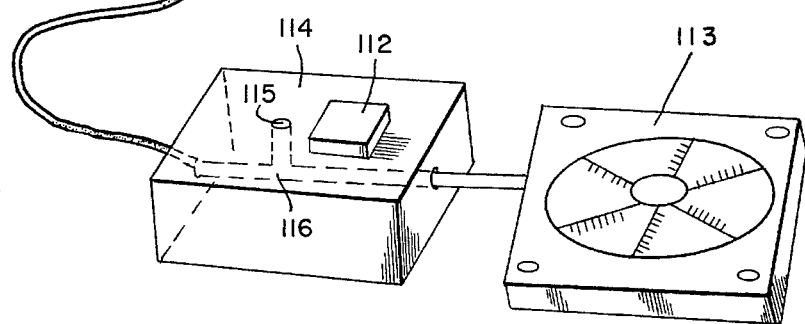
FIG. 16

MONITOR OF LOW PRESSURE INTERVALS WITH CONTROL CAPABILITIES

BACKGROUND OF THE INVENTION

This invention relates to a monitor of pressure intervals with control capabilities that can provide data obtained from either the detection of very low positive, negative or differential pressures that can be used to control devices having uses in health care and industry.

Originally the primary purpose was to develop a sensor that could detect the very low negative pressure occurring at the nasal passageways, in order to monitor respiration.

A simple way was developed for doing this and U.S. Pat. No. 4,878,502, Nov. 7, 1989, was issued. This sensor consisted of a very low density ball moving in a transparent tube with its position being optically sensed. However, due to the very low density of the ball, it was attracted by static and the forces of cohesion to stick to the tube. To eliminate this sticking to the tube it was necessary to coat the ball with graphite. The graphite created a conductive coating to prevent the static attraction, but its main purpose was to put a coating on the ball that prevented the very few electrons in the low density ball being attracted to the much denser electrons in the plastic tube by the forces of cohesion.

This made possible an inexpensive device that could detect when apnea occurred (failure to breath for 10 seconds or longer) and was suitable for use as a monitor for possible prevention of crib-death (SIDS). However, in use it was best if a filter was used to prevent the possibility of the graphite powder being ingested. This reduced the sensitivity and with the fact that the ball could last for approximately 100,000 operations (when it would require refurbishing) it was not too suitable for health care use. The device was found to be better suited for industrial use. Its industrial use is to detect airflow (example: act as a safety interlock switch to detect loss of airflow in air cooled electronic equipment) and other uses such as to detect the low pressure maintained in clean rooms to prevent the entrance of contaminated air. In industrial applications where the equipment had the switch working only when the equipment was turned on or off once a day, a life of 10,000 operations would be the normal requirement and the 100,000 operations of the plastic ball's operating life was extremely satisfactory. A filter is not required for industrial applications so the sensitivity is high.

When the previous device was used for detecting apnea in infants to prevent crib-death (SIDS), it was necessary for the device to be connected to the infant's nasal cavities by the use of a nasal cannula normally used for administering oxygen.

A simpler way was developed so it would not be necessary to subject the baby to wearing a nasal cannula. This simpler way was for the baby to wear the pneumatic breathing belt sensor with minimum space maintaining tapes, U.S. Pat. No. 4,602,643—Jul. 29, 1986. The use of the belt overcame the requirement that a filter be used, and it, therefore, made it possible to use the maximum sensitivity of the ball type sensor.

The limited number of operations of the ball type sensor required that a more satisfactory sensor, with a longer operating life, be developed. This resulted in a sensor employing a diaphragm being created that detected the movement of the diaphragm by the use of optoelectronics. This device had excellent sensitivity and U.S. Pat. No. 4,745,925, May 24, 1988, was issued for this device. This device not only sensed the low negative pressure of inhalation, but eliminated the need for a filter, and had a life of over 10 million operations. The patent also described its use for inhalation therapy, where each time a breath is taken it triggers a dose of oxygen. The dose of oxygen was for a fixed period of time, adjusted manually. The use of intermittent flow of oxygen over the normal continuous flow can result in 50 to 70% savings in the cost of oxygen. This is possible since a human inhales approximately 30% of the time and exhales 70% of the time; 30% of the oxygen goes into the patient and the other 70% goes into the room and is wasted.

It was found that this unit operated satisfactorily in the day time when the patient was breathing through his nose. However, during sleep the patient could breath through his mouth and this reduced the negative pressure so much at the nasal cavities that it could not be sensed by the optoelectronic sensor.

This led to a development of a mouth nose mask, U.S. Pat. No. 5,005,517—Apr. 9, 1991, that provided for diversion of some of the oral inhalation air to the nasal passageways where it could be sensed by a nasal cannula connected to the monitor employing the optoelectronic sensor.

U.S. Pat. No. 5,024,219—Jun. 18, 1991 shows how the above developed unit, U.S. Pat. No. 4,745,925—May 24, 1988, can have multiple uses such as being used from four possible sources of supply; a large tank of breathable gas, a small tank of breathable gas, a wall outlet supplied from a bulk storage system of breathable gas, and an oxygen concentrator supplying oxygen from ambient air.

All of the above used a fixed dose of oxygen that had to be manually adjusted, U.S. Pat. No. 5,038,771—Aug. 13, 1991 was issued for a new developed method where the dose of oxygen was determined by taking a percentage of a previous breath, thus automatically adjusting to a rate of breathing of air-breathing animals, including humans.

In an effort to create a sensor that could be manufactured at lower cost, a capacitance sensor, U.S. Pat. No. 5,052,400—Oct. 1, 1991 was developed.

Further development made it possible for a single monitor to sense respiration by use of a nasal cannula or a pneumatic breathing belt. This made it possible for the best method to be selected, at the bedside, for utmost patient comfort, and for which U.S. Pat. No. 5,074,299—Dec. 24, 1991 was issued.

The experience gained from the development of the above products resulted in an effort to develop a device that would have greater sensitivity, lower cost, unlimited control capabilities, longer life, smaller size, and the ability to be programmed to the special requirements of an unlimited number of applications. This resulted in the development of the monitor for low pressure intervals with control capabilities as explained in the summary of this invention, that can do all the past functions and many new sophisticated functions because it is software controlled. It also employs a newly developed vane type sensor that is more sensitive, smaller size, and less costly to manufacture.

When used as a medical device for inhalation therapy, it provides for an intermittent flow of oxygen to save cost while being clinically equivalent to continuous flow now in use. It also provides for a higher quality health care because it can signal if the patient is not receiving the benefit of the therapy.

SUMMARY OF THE INVENTION

This invention can be applied to devices associated with breathing, such as medical devices that can be used as unattended respiration monitors with control capabilities.

Its operation is dependent on detecting the negative pressure present at the nasal cavities when inhalation occurs. This negative pressure can be of a very low value when the air-breathing human is breathing through his mouth.

It is possible to obtain sufficient negative pressure that the invention can monitor, by using the common nasal cannula used for administering gaseous fluids when the patient breaths through his nose. However, when the patient breaths through his mouth, this lower negative pressure makes it almost impossible to detect the onset of inhalation at the nasal cavities.

To overcome this problem, a mouth-nose mask was developed, described in U.S. Pat. No. 5,005,571. This mouth-nose mask provided for the diversion of some of the oral inhalation air to the nasal cannula to sense inhalation.

The use of this mouth-nose mask, with the nasal cannula used for administration of gaseous fluids, provided for successfully sensing the negative pressure of inhalation when the patient breathed through his mouth. However, it was uncomfortable to wear compared to the simple nasal cannula. Therefore, a special nasal cannula was developed for the purpose of sensing respiration. This nasal cannula provided for a much lower impedance to the flow of negative pressure from the nasal passageways.

A patent application has been filed covering the nasal cannula for sensing. This nasal cannula for sensing provides for obtaining enough negative pressure to operate the invention's respiration monitor when the patient breaths through his mouth or nose.

The sensor described in this patent application is capable of detecting negative, positive, or differential pressure of 0.001 ounce per square inch, or more, but has it's sensitivity adjusted to 0.0017 ounce per square inch in this use as a respiration monitor to make it less sensitive to stray movements in the tubing connecting the two prongs entering the nasal cavities to the inlet of the respiration monitor. The 0.0017 ounce per square inch of negative pressure sensitivity provides for sensing the low negative pressure at the onset of inhalation, when breathing through the nose or mouth takes place, using the newly developed nasal cannula for sensing.

When the invention uses its control capabilities for inhalation therapy, the nasal cannula for sensing is used for two functions, one to detect the negative pressure of inhalation, two to administer the therapeutic gas. However, it is possible to only use a single function at a time.

It is, therefore, necessary to use the control capabilities of the invention to use it for inhalation therapy. The invention's monitor obtains data as to the number of breaths per minute, length of the breath, length of inhalation, and length of exhalation. It uses this data to determine the length of dose.

Air-breathing humans inhale approximately 30% of the time and exhale approximately 70% of the time. Therefore, 30% of the inhalation gas goes into the patient and the other 70% goes into the environment and is wasted because there is a continuous flow of the therapeutic gas in present day systems.

The invention, in this use, supplies therapeutic gas only during the time of inhalation and saves 50 to 70% of the cost of the therapeutic gas.

However, the chief advantage is not in the cost savings, but the fact that it monitors the patient and will give an audible and visual alarm if the patient is not receiving the benefit of the therapy.

The therapy given by this use of the invention results in an intermittent flow of the therapeutic gas that is clinically equivalent to the continuous flow systems now in use.

It can save lives because it prevents the tragic errors that can occur when a doctor prescribes a dose of oxygen, which fails to be inhaled by the patient because of a misplaced cannula or stuffed nose, resulting in a blood test that shows low oxygen content. The doctor unknowingly fails to realize that the oxygen is low because the patient was not getting the benefit of the therapy. He increases the administration of the oxygen, and the patient now obtains the full benefit when someone corrects the reason for the previous failure of the patient to receive the full dose.

Tragedy can now happen because the patient can receive too much oxygen that may result in death, as oxygen in large doses can be toxic and cause lung failure.

To properly operate the sensor used in this invention, it is necessary to always have a pressure supplied to it. When it is used in inhalation therapy the pressure of the gas being administered can be used. However, if the device is used only as a monitor for respiration, the necessary pressure can be obtained from a miniature brushless blower.

When the invention is used only as a respiration monitor, it has the advantage of no electrical connections to the patient. The only connection to the patient is the air tubing connecting the two prongs in the nasal cannula (for detecting the negative pressure of inhalation) to the input connection of the monitor. Therefore, it is impossible to have any electrical hazard to the patient. Thus, the monitor can be used with magnetic resonance imaging, to detect respiration, where there can be no electrical wiring to the patient.

Other monitoring methods, such as pulse oximetry measurements which are considered to be risk-free, have been reported by Sloan[1], and Murphy, Secunda, and Rockoff[2] as having caused severe burns on the fingers of patients.

1. Sloan T: Finger injury by an oxygen saturation monitor probe. Anesthesiol 1988; 68:936–938
2. Murphy K. G., Secunda, J. A. Rockoff, M. A: Severe burns from a pulse oximeter during MP 73:350–352

The respiration monitor controlling the administration of therapeutic gas can also be used in giving inhalation drugs to a patient by nebulizer. At present many doctors avoid the use of drugs by nebulizers as the dose received by the patient is dependent upon his ability to inhale it while there is a continuous fog of the drug being discharged. Using the invention for this purpose results in the drug only being dispensed when the patient inhales and none is lost when the patient is exhaling. Thus whatever is gone from the nebulizer supply cup has been the actual dose given to the patient.

The unit described for inhalation therapy can also be used for administering air from air tanks used by firemen, pilots and passengers flying in private aircraft above 14,000 feet, and by people in areas subject to extremes of air pollution. An air tank that holds 400 liters of air, which was being used at 2 liters per minute, would last for 200 minutes, but by using the invention would last for 10 hours.

The same unit used in a hospital for inhalation therapy can also function as a respiration monitor because the serial port from the micro-controller chip, connected by cable to the communication port of a central computer, and can be used for constant surveillance of unattended patients in general care.

Using the monitor for general care does not necessitate that it be delivering a gaseous fluid, for when used in this manner, a very small blower having a pressure of 0.1 ounce per square inch, will allow it to be used simply as a respiration monitor.

Hospitals purchasing the unit for inhalation therapy will have its cost amortized by the saving in oxygen cost while increasing the quality of health care by assuring that the patient is receiving the full benefit of the therapy. The same unit can then be connected, along with other like units, to a central computer where there can be constant surveillance of the data given by the monitors.

This constant monitoring can help prevent avoidable death that often occurs in the nighttime when patients are not physically observed for long periods of time.

A unit having the functions previously described for inhalation therapy can also be used for the administration of anesthesia gaseous fluid. Often when nitrous oxide (laughing gas) is being administered to a patient having dental work done, a loose fitting mask can cause a loss of the gas into the environment. Studies disclosed when this leaking gas is inhaled by people working with the patient it can have disastrous effects on pregnant women and lower the sperm count of men, making it more difficult to create offspring. Since the invention would administer the nitrous oxide only when the patient inhales, the loss of the anesthesia into the environment is prevented.

Still another use for the invention is its use as a treatment for obstructive sleep apnea. In obstructive sleep apnea, the most frequent reason for difficulty is excessive relaxation, during sleep, of muscles of the soft palate at the base of the throat, and the uvula. These sagging muscles obstruct the airways. An effective treatment is to force into the nasal passages and into the airways a continuous positive airway pressure to keep them open when apnea is detected.

Impedance pneumography that has been utilized by monitoring manufacturers for more than 20 years has been found in studies[3][4], not to be a reliable method of detecting apnea caused by upper airway obstruction.

3. Warburton D. Stark A, Taeusch H. W.: Apnea monitor failure in infants with upper airway obstruction. Pediatrics 1977; 60:742–744
4. Brouillette R. T., Morrow A. S., Weese-Mayer D. E., et al: Comparison of respiratory inductive plethysmography and thoracic impedance for apnea monitoring. J. Pediat 1987; 111:377–383

The monitor described in this application detects the very low negative pressure of the onset of inhalation, which is only 0.0017 of an ounce per square inch, and will immediately detect if breathing stops, and is the most reliable way of detecting apnea caused by upper airway obstruction.

The respiration monitor can detect when apnea (breathing stops for 10 seconds or longer) occurs. At this time a visual and audible alarm will sound. This alarm circuit also can be used to actuate a continuous positive airway pressure to be delivered through the nasal cannula (for sensing) that would open up the airways.

The past examples given have been for health care uses. However, it should be understood that the primary use of this invention is to monitor pressure intervals and use the data obtained for controlling. It should also be understood that it can be used in industry, polluted areas, aeronautical, subterranean, or underwater environments.

An example of industrial use is in the manufacture of integrated circuits where it can be used to detect the presence and position of a very low weight chip.

The position or presence of a chip can be determined by drilling a small hole on the surface on which it is resting. To this small hole a connection is made with tubing to a "T" connection. One connection to the "T" is a low negative pressure obtained from a very small brushless blower. A second connection is made to the drilled hole, and the third connection goes to the inlet connection to the input of the monitor. When the part covers the hole, a negative pressure actuates the sensor (by moving the vane of the capacitance sensor from the normal position.) When this occurs, a positive pressure enters the sensor and the vane is returned to its normal position ready to detect if there is again a negative pressure indicating if a part is there. If no negative pressure is present, the micro-controller chip can be set to give a signal indicating there is no chip present or in position to close up the hole.

The foregoing, and other objects, features, and advantages of the invention are now apparent and the drawings and preferred embodiments will aid in a further understanding of the invention.

BRIEF DESCRIPTION OF THE DRAWINGS

Brief descriptions of the drawings are given below; note that reference characters refer to the same parts throughout the various views. Other features and objects of the monitor of low pressure intervals with control capabilities will be understood from the claims and appended drawings in which:

FIG. 11—is a diagrammatic view of how the monitor is connected from the oxygen source to the nasal cannula for inhalation therapy use.

FIG. 12—is a diagrammatic view of how the monitor is connected for use as a respiration monitor for unattended monitoring of patients in general care.

FIG. 15—is a diagrammatic view of how the monitor can be used as an assist controller to sense inhalation and to deliver a volume-limited breath for short-term ventilatory support for post operative care.

FIG. 16—is a diagrammatic view of how the monitor can be used in industry to detect the presence of low weight parts.

DESCRIPTION OF THE PREFERRED EMBODIMENTS

Figure 1:
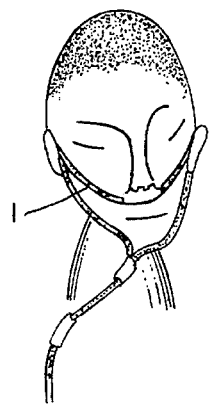
FIG. 1—is a view of a patient wearing a nasal cannula.

The foregoing, and other objects, features, and advantages of the invention are now apparent from the following particular description of one of the preferred embodiments, as illustrated in the accompanying drawings in which reference characters refer to the same parts throughout the various views. The drawings are not to scale, emphasis instead being placed upon illustrating the invention.

The sensor described in this patent application has been tested for over 400,000,000 operations without failure.

The invention of this monitor makes it possible to reduce the size and weight making the device lighter for portable use.

The circuits used in this monitor extend battery life, and provide an indication when the battery needs replacement or recharge.

Using a micro-controller chip reduces the parts count for lower cost, makes possible greater effectiveness and safety, while increasing reliability of the device. The use of signal processing and data display provides for this technology of microprocessor to control the monitor's coordinated data transfer and establishes the operating sequences.

The monitor can be used for research as it has the capability of interfacing to an external terminal such as a personal computer, for the purpose of studying a patient's activity during oxygen therapy. Data taken by the monitor at the patient's bedside can be sent to a remote computer by use of the serial port provided on the back panel of the monitor. The monitor has safety features such as a flashing red light and an audible alarm, actuated when the patient fails to inhale oxygen for 20 seconds.

The monitor is provided with an internal battery providing for a minimum of 8 hours of continuous use.

The monitor described in this embodiment has full clinical equivalency to the present method of continuous flow, but due to the fact that it provides for intermittent flow determined by a patient's breathing, it can save 50% to 70% of the cost of oxygen.

This invention monitors the patient, and provides an alarm if the patient is not receiving the benefit of the therapy. The monitor turns on oxygen as soon as three inhalations are detected by the sensor. Ideally, it should turn oxygen off when inhalation ends. However, since a nasal cannula is used to both sense and deliver oxygen, it can only be used for one of these functions at a time. It is, therefore, necessary to compute the expected inhalation many times when the dose function prevents the sensing function from taking place. The micro-controller chip used in this monitor is effective in determining the correct dose of oxygen because it is software controlled and can use a number of methods for computing the expected duration of inhalation.

The monitor provides three methods for computing the expected inhalation duration. The simplest method uses a fixed dose, either 0.2 or 0.5 seconds for each inhalation.

The second method uses a fixed percentage of the expected breath duration as the inhalation duration. The fixed percentage (10, 20, 30, 40, or 50%) must be prescribed by a licensed physician. If an inhalation duration computed in this way is less than 0.2 seconds, the monitor increases it to 0.2 seconds. In the monitor the median value of the three previous breath durations is used to determine the expected breath duration.

The third method is the most sophisticated technique and is similar in principle to the second method. It automatically tracks the percentage of the expected breath duration used as the inhalation duration. This requires a prediction of the current breath duration, since the nasal cannula can only sense the beginning of inhalation when no oxygen is being delivered. As in the second method, the monitor uses the median (which is the length of the breath between the shortest and longest breath) of the three previous breath durations. It then automatically tracks the percentage of the expected breath durations used as the length as follows:

If the end of inhalation is detected after oxygen dose is turned off, dose was too short. In this case the correct percentage of the expected dose can be computed exactly since the length of inhalation and full breath are known. If the expected percentage of dose is greater than 50% of the expected breath, the monitor decreases it to 50%.

If the oxygen dose is still on after inhalation ended, oxygen dose was too long. An adjustment is made to reduce its length by multiplying the length of time of the dose by some number less than one (0.9) for each of the following doses until the end of the dose occurs at the end of inhalation. This automatic operation relies on the fact that the dose does not change much from one breath to the next, and the average length of the dose closely approximates the average length of inhalation. Thus the minimum saving is 50%, with possible maximum savings being 70%, in the cost of oxygen.

The following information describes the operation, circuits used, and construction features of the monitor.

Figure 2:
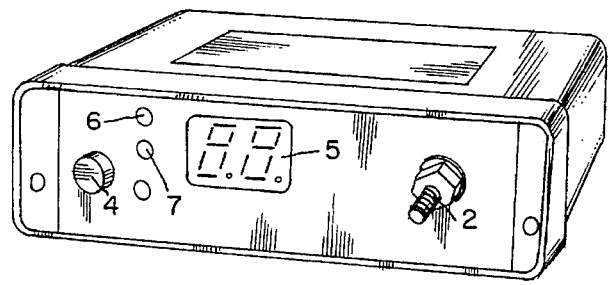
FIG. 2—is a diagrammatic front view of the monitor.

A patient is connected to the nasal cannula, FIG. 1, or a similar device, and the other end of the cannula is attached to an outlet connection 2, FIG. 2 of the monitor. The nasal cannula 1 is used for the dual purpose of sensing an inhalation by detecting the negative pressure at the nostril of patient, and for delivering a dose of oxygen that is triggered when inhalation is sensed. This dose is automatically adjusted in accordance with the rate of breathing as well as the length of breath.

Figure 3:
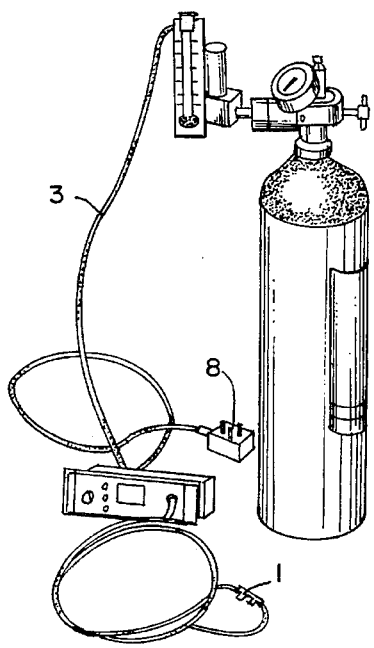
FIG. 3—is a diagrammatic view of a complete system using the monitor.

The monitor is connected by tube 3, FIG. 3, to an adjusted regulated flow of oxygen (such as 2 liters per minute) from a tank, oxygen concentrator, or a wall outlet in a hospital using a fixed regulator, to obtain a fixed pressure of 20 or 50 pounds per square inch, and a second regulator adjustable to zero pounds per square inch.

Before powering up the monitor, it is necessary for the flow of oxygen to be adjusted to the desired flow rate at the source of supply. Oxygen will then pass through the monitor as a continuous flow directly from tube 3, FIG. 3 to outlet connector 2, FIG. 2, through nasal cannula 1, FIG. 3, that supplies oxygen to a patient.

Powering up the monitor by pressing switch 4, FIG. 2, to an "on" position will turn an apparatus "on", which will be verified by digital display 5, FIG. 2, being illuminated. Immediately flow of oxygen from connection 2, FIG. 2, will be stopped by the monitor, and no oxygen will flow from outlet connection 2. To obtain a flow of oxygen from outlet connection 2, a negative pressure must be detected from the first three breaths of a patient wearing the nasal cannula.

When this occurs, it turns the oxygen on. Ideally, it would turn the oxygen off when an inhalation ends. Unfortunately, the sensor can only detect an inhalation when the oxygen is off, due to the fact that the nasal cannula 1 is used to sense and deliver oxygen. Therefore, it can't turn the oxygen on and wait to detect the end of inhalation. Instead, it must compute an expected inhalation duration and turn the oxygen off when this period has elapsed.

Three methods for computing an expected inhalation duration are implemented in the monitor system as previously described.

The LED (light emitting diode) 6, FIG. 2, marked "Dose" will indicate when oxygen flows. The monitor is always shipped prepared for automatic operation. Other modes of operation should be made only by an authorized service representative upon the request of a licensed physician.

The LED (light emitting diode) 7, FIG. 2, marked "AL" will indicate when the nasal cannula becomes disconnected from a patient or the sensor becomes insensitive. When this occurs, LED 7, FIG. 2, will intermittently flash and an audible alarm 75, FIG. 10, will be sounded if oxygen is not delivered for 20 seconds. This is a safety feature which will activate the front panel display 5 to indicate the number of seconds, up to 64 seconds, that have elapsed since failure of oxygen delivery. After 64 seconds, the panel will display "El" until a breath is sensed or power is momentarily turned off.

The monitor should not be powered up and left unused as this consumes more power than when it is in use.

Figure 4:
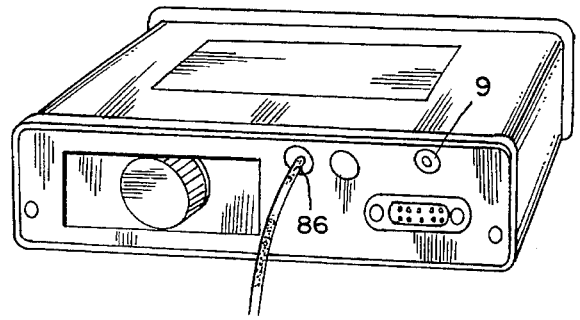
FIG. 4—is a diagrammatic rear view of the monitor.

The monitor can be operated from a 120 volt AC wall outlet by use of a 9 volt wall power supply 8, FIG. 3, plugged into Jack 9, FIG. 4.

The monitor can be operated from any 12 volt DC supply; such as from a car battery. A special connecting cable from the car's cigarette lighter is required.

The monitor has three outstanding features. One is that it can save 50% to 70% of the cost of oxygen. The second is that it will indicate when the patient is not receiving the benefit of the therapeutic oxygen. Thirdly, data can be obtained from the monitor for research use.

Following describes the sensor used in the monitor for sensing an inhalation of a patient.

Figure 5:
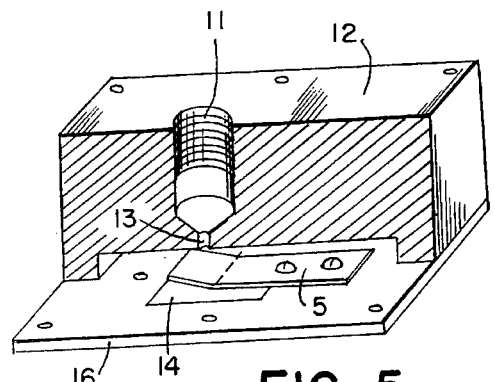
FIG. 5—is a diagrammatic view of the vane type capacitance sensor, with it's aluminum block shown by A—A cutaway to expose the vane actuated by the negative pressure of inhalation.
Figure 6:
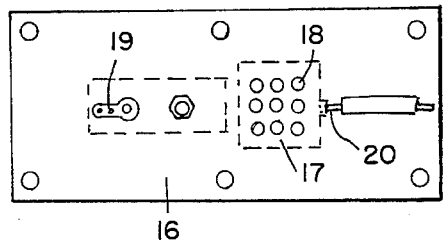
FIG. 6—is a bottom view of the printed circuit board used for mounting the moving parts of the sensor.

FIG. 5 is a cutaway isometric drawing of the sensor. A standard ¼" pipe thread 11, FIG. 5, is shown cutaway through its center located in an aluminum block 12. Into this threaded pipe hole is inserted connector 2, FIG. 2, used for connecting the monitor to the patient's cannula 1, FIG. 3. When a patient inhales, a negative pressure occurs at the small hole opening 13, FIG. 5. This negative pressure causes a 0.0003" aluminum coated mylar vane 14, FIG. 5 to be sucked up and hit the bent up portion of the two hole clamping bracket 15, FIG. 5. Vane 14 has its aluminum coated side facing upward and its insulated side adjacent to copper foil 17, FIG. 6, outlined with a dotted line on a printed circuit board 16, FIG. 6. FIG. 5 shows the printed circuit board 16 facing up and FIG. 6 shows the bottom of board 16. The two plate capacitor is formed by vane 14 and copper foil 17 with the dielectric being the 0.0003" thick mylar. Vane 14 can be sucked upward because there are 9 holes, 18, FIG. 6, under vane 14 to allow atmospheric pressure to force vane 14 upward when there is a negative pressure at hole 13.

Electrical connection 19, FIG. 6, is made by clamp 15 clamping vane 14.

Electrical connection 20 is made by a wire soldered to copper foil 17. These two electrical connections make vane 14 a variable capacitor whose operation is dependent upon the inhalation of patient wearing nasal cannula 1. The value of capacitor is inversely proportional to the distance between the two plates and has a value in the pico-farad range. Voltage applied to this capacitor is kept constant. The change in charge is determined by the position of vane 14 relative to copper foil 17.

Figure 7:
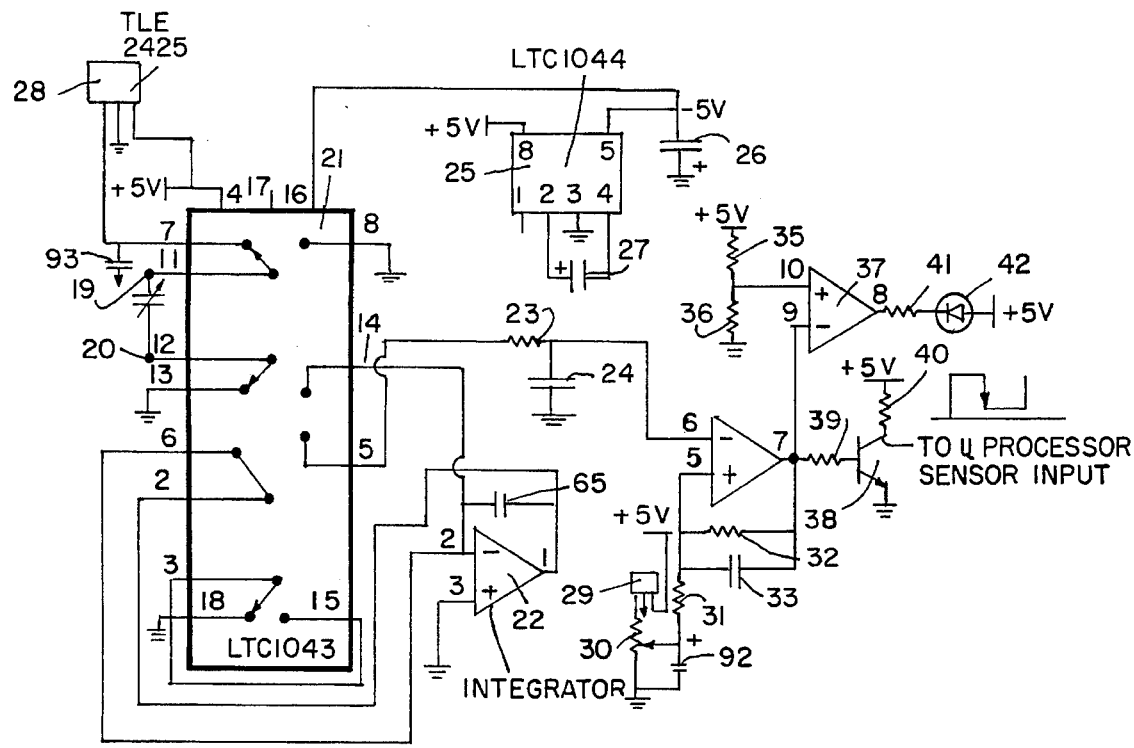
FIG. 7—is a schematic diagram used to describe the electrical operation of the sensor and it's power supplies.

FIG. 7 is a circuit diagram used with an inhalation sensor. The sensor is connected to the circuit by electrical connections 19 and 20. Integrated chip 21 is a monolithic, charge-balanced, dual switched capacitor instrumentation building block which continuously charges and discharges the sensor connected to connections 19 and 20. Chip 21 generates an internal two non-overlapping clocks, phases 1 and 2. During phase 1, internal switches are connected in such a manner that the sensor's capacitance is charged to q=CV and during this phase, the integrating capacitor of the integrating system of chip 21 is shorted for the purpose of discharging. During phase 2, charge accumulated on the sensor's capacitance is dumped on capacitor 65. Output of integrator 22 is connected to output of chip 21 at pin 5 which is filtered through an RC low pass filter using resistor 23 and capacitor 24 as shown in FIG. 7. The monitor requires a negative, as well as a positive, power supply which is provided by switched capacitor voltage converter 25 of FIG. 7 and capacitors 26 and 27 are used to stabilize 25. The capacitors 92 and 93 are used to bypass high frequencies to the ground.

Virtual ground chip 28 generates a 2.5 V reference voltage used by pin 7 of chip 21. Virtual ground chip 29 is also used to generate a stable 2.5 V reference for resistor 30. The combination of resistors 31 and 32 with capacitors 33 generates an hysteresis for comparator 34 so that comparator 34 does not oscillate. Resistors 35 and 36 form a voltage divider to generate a reference voltage of 2.5 V to be used by comparator 37 to compare the logic level of comparator 34. Transistor 38 is used to invert the output logic level of comparator 34. Resistor 39 is used to limit the current going to base of transistor 38, while resistor 40 is a pull-up resistor. Resistor 41 is a current limiting resistor to LED 42 which will illuminate every time an inhalation occurs. Output of transistor 38 is fed to the microprocessor.

Figure 8:
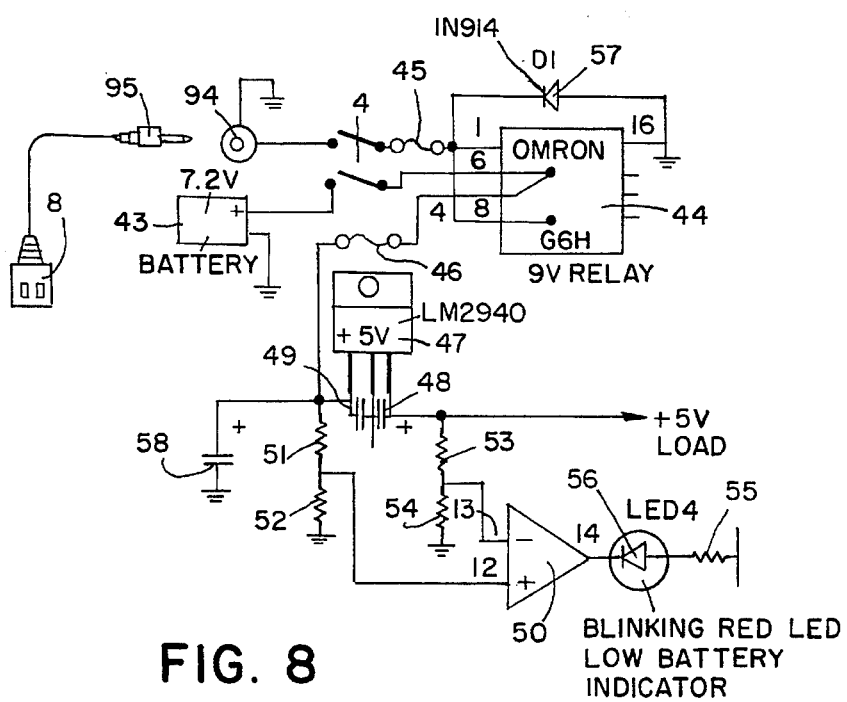
FIG. 8 is a schematic diagram used to describe the electrical operation of the dual power supplies (wall transformer and battery) and low voltage detection circuitry.

FIG. 8 is a circuit diagram of power supply and low battery indicator used in the monitor.

The monitor operates from either 9 volts 500 mA wall power supply 8, FIG. 3, FIG. 8, or from rechargeable nickel cadmium battery 43, that supplies 7.2 volts 1200 mA.

Figure 9:
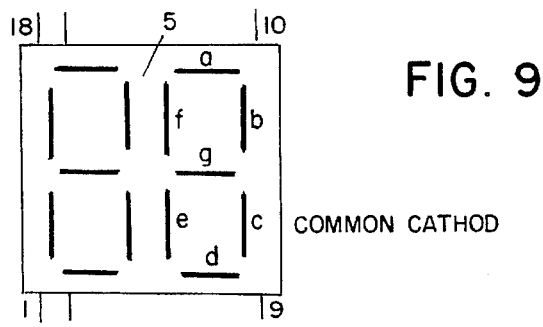
FIG. 9—is a schematic diagram of the electrical connections of the digital display.

Power switch 4 controls the On/Off function of the monitor. Normally wall transformer 8 is connected to a working 120 V AC outlet, and the male jack 95 of FIG. 8 is plugged into power jack 94 on the monitor. When switch 4 is turned "on", relay 44 is energized allowing wall transformer 8 to power up the monitor. Power "on" is indicated by the two seven segment LED 5, FIG. 2, FIG. 9 displaying "8.8" for a fraction of a second, after which it displays the mode of operation selected, until the first inhalation.

In case of AC power failure while switch 4 is "on", relay 44 is de-energized and the monitor automatically switches to second power supply battery 43, if it is installed and fully charged. Relay 44 does not consume any power when this occurs. Power failure of the line voltage is indicated by a momentary blinking of display 5 when switching from wall transformer 8 to battery 43. Once switching is completed, the monitor display 5, FIG. 2, indicates "8.8" for a fraction of a second, and then the mode monitor was operating in before power failure. Display of the mode will disappear when inhalation occurs.

The monitor has fuse 45 protecting circuits from high current drain from wall transformer power supply 8, and fuse 46 protects circuit from battery 43 power supply.

Voltage regulator 47 is used for regulating wall power supply 8 or battery 43 to a constant plus 5 volt source. Capacitors 48 and 49 are used to prevent voltage regulator 47 from oscillating, and filtering of input supply respectively. Battery pack 43 requires a low battery detection system and this is incorporated by using comparator 50 along with resistors 51, 52, 53, 54 and 55, and LED 56 as shown in FIG. 8. Red LED 56 flashes whenever battery 43 voltage goes below set volts. Diode 57 is across relay 44 coil, and capacitor 58 is used to by-pass high frequency signals to ground.

Figure 10:
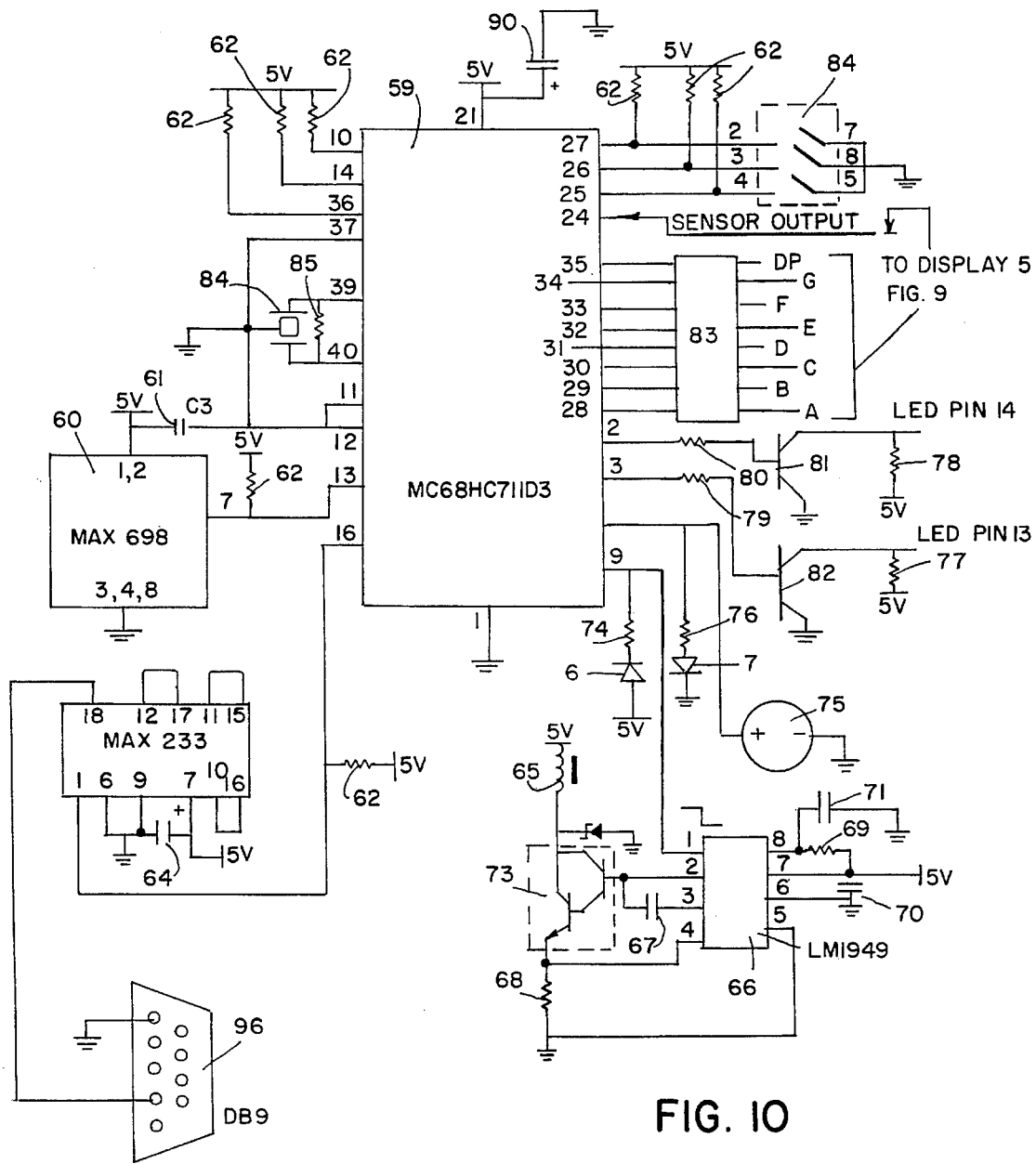
FIG. 10—is a schematic diagram of the electrical operation of the micro-controller chip.

FIG. 10 is circuit diagram for micro-controller 59. Various external integrated chips are necessary for the proper operation of micro-controller 59. Chip 60 is a "Power-on reset" which monitors the +5 V supply in micro-controller 59, and provides a reset during powering up and shutting off the monitor. Capacitors 61 and 90 are bypass capacitors to suppress any glitches in the power supply. Resistor 62 is a pull-up resistor. Integrated chip 63 is an RS232 transmitter and receiver for the purpose of communicating the external systems, such as personal computers. Capacitor 64 and resistor 62 are used for bypassing and pull-up respectively.

In order to control the flow of oxygen for a duration of time, an oxygen valve is used which is opened and closed by using internal solenoid 65. A solenoid is a power consuming element. It takes more power to activate a solenoid than it does to keep it energized. Once it is energized it takes 3 to 4 times less power to keep it energized. In monitor, chip 66, along with components capacitance 67, resistors 68 and 69, capacitance 70 and 71, zener diode 72, and darlington transistor 73, are incorporated to reduce the total power consumption by the solenoid 65 as shown in FIG. 10.

Components capacitor 71 and resistor 69 are used to form an RC timing circuit to provide a high dose of current during the initial energizing of solenoid 65, and after this time constant the current is reduced just enough to hold solenoid 65 closed. Zener diode 72 limits voltage to solenoid 65. Darlington transistor 73 is used for driving solenoid 65.

Distribution of oxygen by solenoid 65 is indicated by green LED 6, Resistor 74 is used to limit current to LED 6.

A second safety feature incorporated in the monitor, is the red flashing LED 7, and alarm 75. Resistor 76 is used to limit the current to LED 7. In normal operation the time between inhalations is shown on display 5 in seconds. Every time the sensor detects an inhalation the count on the display is reset to "00". For example, if a patient inhales, display will show "00", and will increment at a rate of one second, "01", "02", "03", "04", "00". This example shows the second inhalation was taken after 4 seconds. If nasal cannula becomes displaced, or sensor fails to indicate inhalation, counter will keep incrementing until 20 seconds (a value that can be software changed at the factory). At the end of the 20 seconds it will activate flashing red LED 7 and alarm 75 until the next inhalation is detected or unit is reset by turning off the monitor. If unit is not reset or inhalation is not detected, counter will keep incrementing until 65 seconds, when display 5 will show "EI" and remain there until the unit is reset by either turning power off or detecting an inhalation.

Components resistors 77, 78, 79, and 80; with transistors 81 and 82, all work to control the enabling of display 5. All eight resistors 62 are a resistor network that is used as pull-up resistors. The resistor dip pack 83, consists of current limiting resistors to display 5, FIG. 9.

Chip 84 is an SPST sliding switch for selecting various modes of operation of the monitor. The clock necessary to drive the micro-controller chip 59 is generated by crystal oscillator 84 and resistor 85.

FIG. 11 shows how sensor 16 is used for respiratory therapy. Cannula 1, commonly available in hospitals for administering oxygen, is used to connect the flow of oxygen from a user's nostrils to sensor 16 by means of connector 2.

Tubing 87 connects to connector 88 which is internally connected to sensor 16 and provides a positive pressure to return vane 14 to its original position after an inhalation occurs.

The other end of tubing 87 is connected to valve 65. Valve 65 is normally open, so if power fails oxygen will flow continuously. The one unused outlet is sealed close. Tube 89 connects valve 65 to panel connector 86, which is located on rear panel of the monitor. Tube 3 goes from connector 86 to the source of regulated flowing oxygen.

The monitor may be connected to a computer by using serial port 96 and using a cable connected to the communication port of the computer. The monitor will transmit data when the necessary software (i.e. Lotus Works or any communication software) is launched on the computer and the monitor is powered up.

The first data that appears at the terminal will show what mode was selected by the DIP switch 84, FIG. 10 located internally in the monitor. In the following example the fixed percentage selected was 30%.

After the first inhalation the output for this mode will appear as follows:

>B:340EB:OI:228 A:0
>B:1974EB:OI:407 A:200
>B:3897EB:34OI:200 A:200 the definitions for this output are as follows:

B: actual breath length in milli-seconds (mS)

EB: expected breath length calculated by algorithm in mS

I: inhalation time in mS

A: dose of oxygen given for post inhalation in mS

The first inhalation is not displayed on the screen. The second inhalation is the first one displayed on the screen with A:O (no flow of oxygen). The oxygen dose for the third inhalation shown as the second line above is 200 mS and this is always a constant time. The future oxygen dose is calculated by taking the expected breath and multiplying it by 30% (the mode selected.) If the result is less than 200 mS, the oxygen dose will be increased to 200 mS. If the calculated dose is greater than 200 mS the oxygen will be the calculated value.

This method is not valid if constant doses such as 0.2 and 0.5 are used, for then the dose is constant and independent of the breathing rate.

The monitor is most likely to be used with the internal DIP switch 84 set for automatic operation. However, when requested by a physician, other modes of operation can be selected by setting the switch as follows:

| SWITCH POSITIONS | | | | |
| --- | --- | --- | --- | --- |
| 1 | 2 | 3 | 4 | MODE |
| * | off | off | off | 10% |
| * | off | off | on | 30% |
| * | off | on | off | 50% |
| * | off | on | on | 0.2 sec. |
| * | on | off | off | 20% |
| * | on | off | on | 40% |
| * | on | on | off | automatic |

-continued

| SWITCH POSITIONS | | | | |
|---|---|---|---|---|
| 1 | 2 | 3 | 4 | MODE |
| * | on | on | on | 0.5 sec. |

While the invention has been particularly shown and described with references to the preferred embodiments thereof, it will be understood by those skilled in the art that various alterations in form and detail may be made therein without departing from the spirit and scope of the invention. For example, where use with oxygen is described, it should be understood that any gaseous fluid, such as air, or anesthesia gaseous fluids can be substituted.

Moreover, while the invention has been particularly shown and described for clinical use (as with human patient, for example), it should be understood the invention may be used in conjunction with gaseous fluid supply for not only administering such gaseous fluids, but can also contain a small self-contained DC brushless motor to supply the positive pressure needed to activate the sensor vane back to its normal position. The sensor can be activated by negative, positive, or differential pressure. It should be understood that the invention can be used to monitor controlling administration of gaseous fluids, sending out data, controlling alarms (such as when apnea occurs), controlling the delivery of continuous positive airway pressure in the above, and in a subject in industrial, polluted areas, aeronautical, subterranean, or underwater environments.

Moreover, the device can be used to sense the presence or position of parts as well as acting as a touch sensor for robotics in industrial applications.

In the monitor in the described embodiment, it can be readily understood that the cannula for sensing greatly improves its ability to detect very low values of negative pressure in the nasal cavity when inhalation takes place.

When the invention is used only as a respiration monitor, it is necessary to only replace the oxygen supply with a DC brushless motor connected to incoming DC voltage, and using the air pressure from this blower to replace the oxygen supply.

FIG. 12 shows how the monitor is connected when it is used as a respiration monitor. Tube 89 is connected to the outgoing pressure delivered by low DC voltage blower 100. The voltage for operating the blower 100 is obtained from positive side of switch 4, FIG. 8 and the negative voltage after it passes fuse 45, FIG. 8.

The monitor shown in FIG. 12 can also be used as a breath holding indicator to signal the proper moment for an operator of X-ray equipment to expose the X-ray film.

The only change required to the unit described in the preferred embodiment is that the embedded software be changed to have the non-breathing alarm be actuated in a short period (such as 2 seconds.)

The person to be X-rayed must wear a nasal cannula. After the unit is turned on, a minimum of three breaths must be taken. As long as the person breaths there is no signal. When he is given instructions to hold his breath, his compliance with this request will be indicated both by a visual and audible signal. The X-ray operator can then expose the film while the signal for holding the breath is being indicated and upon finishing, inform the patient he can again breath. The monitor has the ability to determine when the patient is holding his breath and verifies if the patient is synchronized with the instruction of the technician exposing the X-ray film.

To use the preferred embodiment for inhalation drugs, either an oxygen supply, air from an air compressor, or other source may be directed into the same input connection for the supply selected. The nasal cannula is only connected to the sensor and the oxygen or air would not be connected to the sensor, but go directly from the output tube 101, FIG. 13 of valve 65 to nebulizer 102.

Figures 13B, 13C:
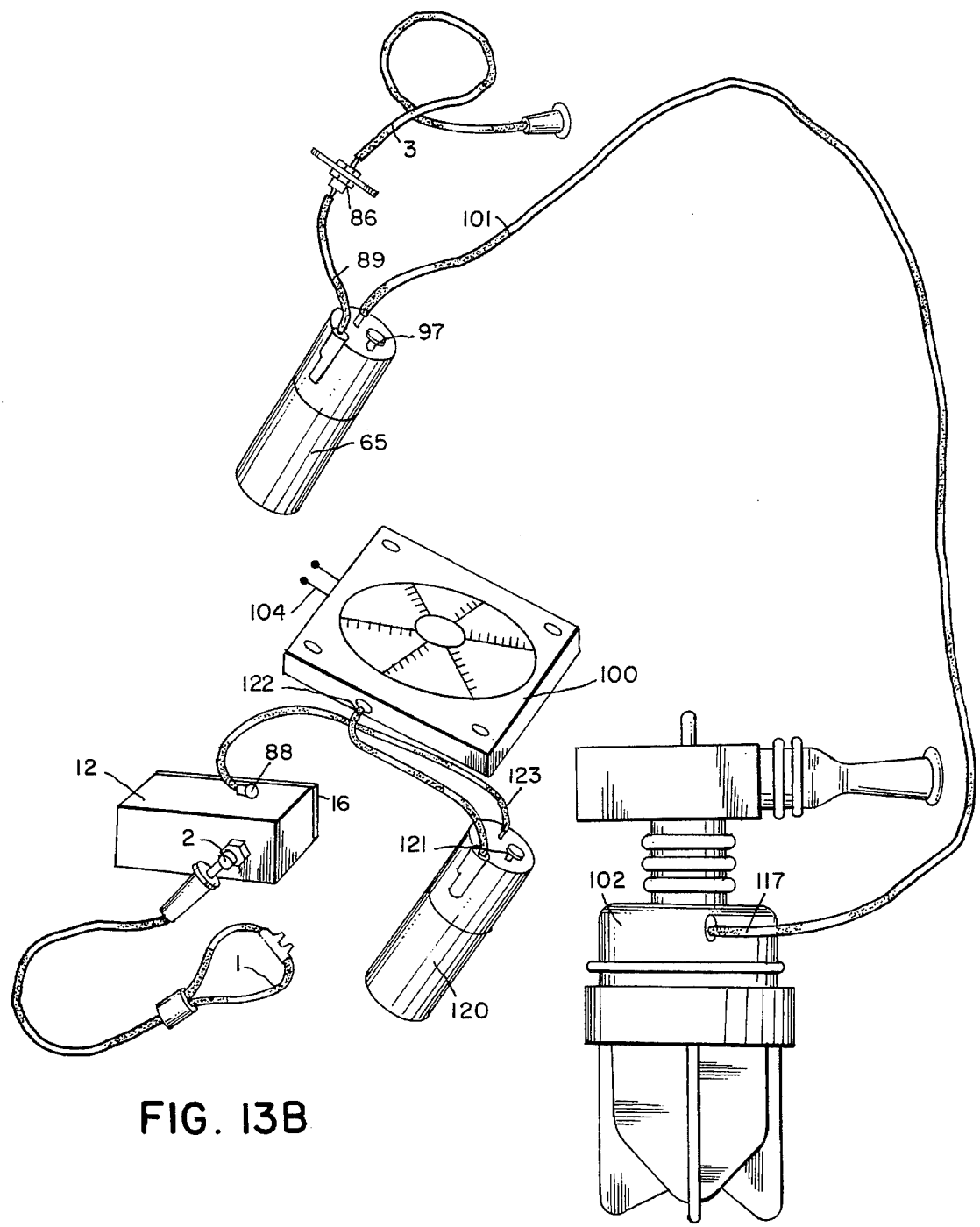
FIG. 13—is a diagrammatic view of how the monitor is connected to dispense drugs by use of a nebulizer, how it can be used with a humidifier, and how it can be used with anesthesia gaseous fluids.

FIG. 13 shows how the monitor is connected when it is used to dispense drugs by use of a nebulizer. Nasal cannula 1 senses the onset of inhalation and triggers a dose of either compressed air or oxygen supplied by tube 3. The small low DC voltage blower 100 replaces the pressure normally supplied by the therapeutic gas (such as oxygen) that is used to return vane 14, FIG. 5 in sensor 12 to its normal position for maximum capacitance after inhalation takes place. The nebulizer atomizes only during the time patient is inhaling, and therefore no drug is atomized when the patient is exhaling; and accurately controls the amount of drug inhaled by the patient. The solenoid valve 120 is wired in parallel to solenoid valve 65. Pressure connection 122, receiving pressure from blower 100, goes through solenoid valve 120 and then through tube 123 to sensor 12.

Administration of anesthesia gaseous fluids can be performed in an identical fashion. Also where an anesthesia gas, such as nitric oxide is used, it can be supplied to tube 3 and delivered to the patient by a mouthpiece replacing nebulizer 102.

If nebulizer 102 is replaced in FIG. 13 at connection 117 by humidifier 119, oxygen will be supplied to humidifier 119 and result in oxygen being delivered to a patient, having enough water vapor added to the inspired gas to make it comfortable.

The monitor can be used for constant surveillance of patients in general care by means of the communication port located on back panel of the monitor, shown in FIG. 4 marked as the serial port.

Administration of anesthesia gaseous fluid can be performed with the unit shown in FIG. 13 in the same manner as oxygen is administered.

To use the monitor for treatment of obstructive sleep apnea only, requires that when the alarm 75 and flashing light 7 indicates an apnea event, blower 105 will be activated by unit 106 to send a constant positive airway pressure for a fixed period of time. At the end of that fixed time the patient would again have the monitor detect if there was breathing. If breathing was restored, the monitor would continue detecting the breathing until an apnea event would again occur, and then it would again activate the constant positive airway pressure from blower 105.

Figure 14A:
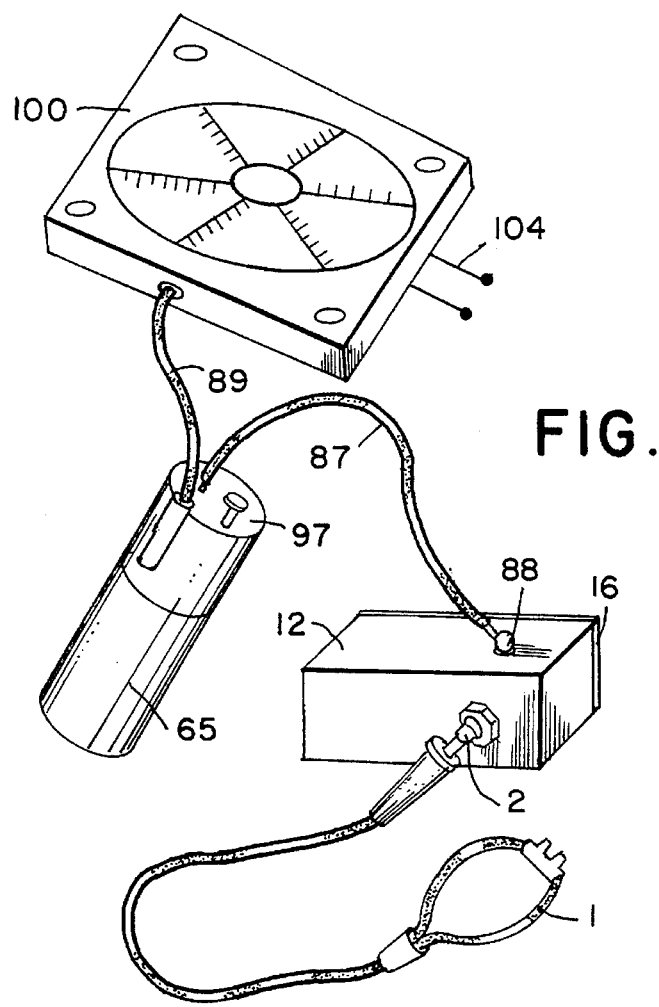
FIG. 14—is a diagrammatic view of how the monitor can be used as an effective therapy for sufferers of obstructive sleep apnea by providing a positive airway pressure when apnea occurs.
Figure 14B:
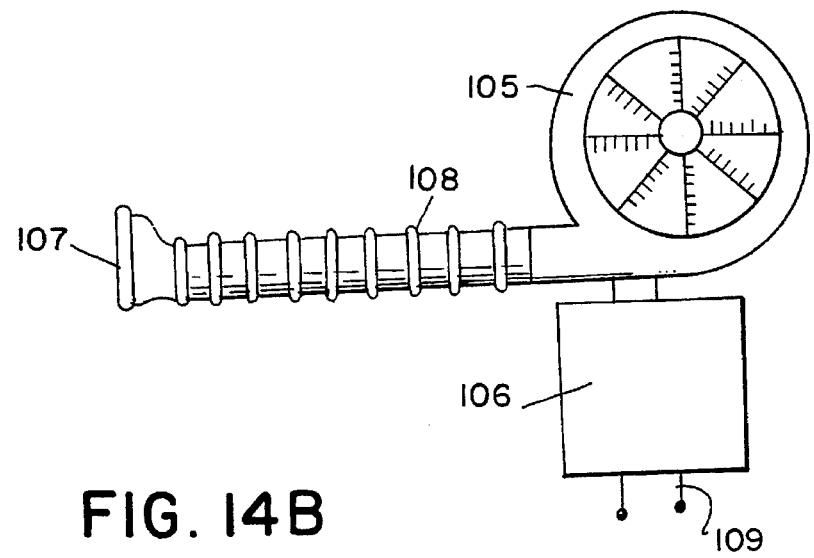

FIG. 14 is a diagrammatic view of how the monitor can be used as an effective therapy for sufferers of sleep apnea. In this application the invention is used as a monitor as previously shown for respiration monitor FIG. 12. When apnea is detected by the respiration monitor, the voltage normally applied to the audio alarm is instead delivered to input 109 of unit 106 that will activate power to operate blower 105 for a length of time. When blower stops at the end of the time, it will remain stopped until the patient has another apnea event. Blower should be able to deliver an approximate maximum of 9 inches of water column and be adjustable to provide a minimum of approximately 1 inch of water column. The pressure provided by the blower is used to deliver a constant positive airway pressure to the patient's nasal passages and into the airways to remove the obstruction caused by the soft palate at the base of the throat, and the uvula. Hose 108 connects the constant positive airway pressure provided by blower 105 to mask 107 which connects to the patient. Nasal cannula 1 is always worn under mask 107 and will only sense apnea when there is no constant positive airway pressure being applied.

To use the monitor for short-term ventilatory support, frequently required for post-operative patients, see FIG. 15. In this application the invention is used as a monitor as previously shown for respiration monitor FIG. 12. At the onset of inhalation the source of pressure support 111 is activated by an electrical signal being applied to terminal 103. The electrical signal for terminal 103 is in parallel with solenoid valve 65, and therefore the pressure support will be given to the patient in the same manner as when used to deliver a dose of oxygen. The patient will always wear the nasal cannula 1, and be connected to the output 110 of the pressure source 111 by means of mouth/nose mask.

FIG. 16 is a diagrammatic view of how the monitor can be used in industry to detect the presence of a low weight part. In this application the invention is used as a monitor with the same set-up as for respiration shown in FIG. 12.

A second blower 113 is used to supply a low negative pressure to a small diameter hole 115. When the negative pressure is escaping from hole 115 no negative pressure is detected at connection 2 of the sensor 12. If a low weight part 112 is in a position to cover hole 115, a negative back pressure is created at connection 2. Thus the presence of part 112 is detected by the monitor and its presence could be indicated by LED 6, FIG. 2. A connection made in parallel to this LED 6 could be used to indicate the part is in position. Using a very short low pressure made available from 1st blower using the mode for a fixed short burst of pressure (such as the switch position for 0.5 sec.) the sensor is reset at the end of the short burst to again detect if part 112 is there. If no part is detected within an encoded time limit the alarm will sound.

Figure 17:
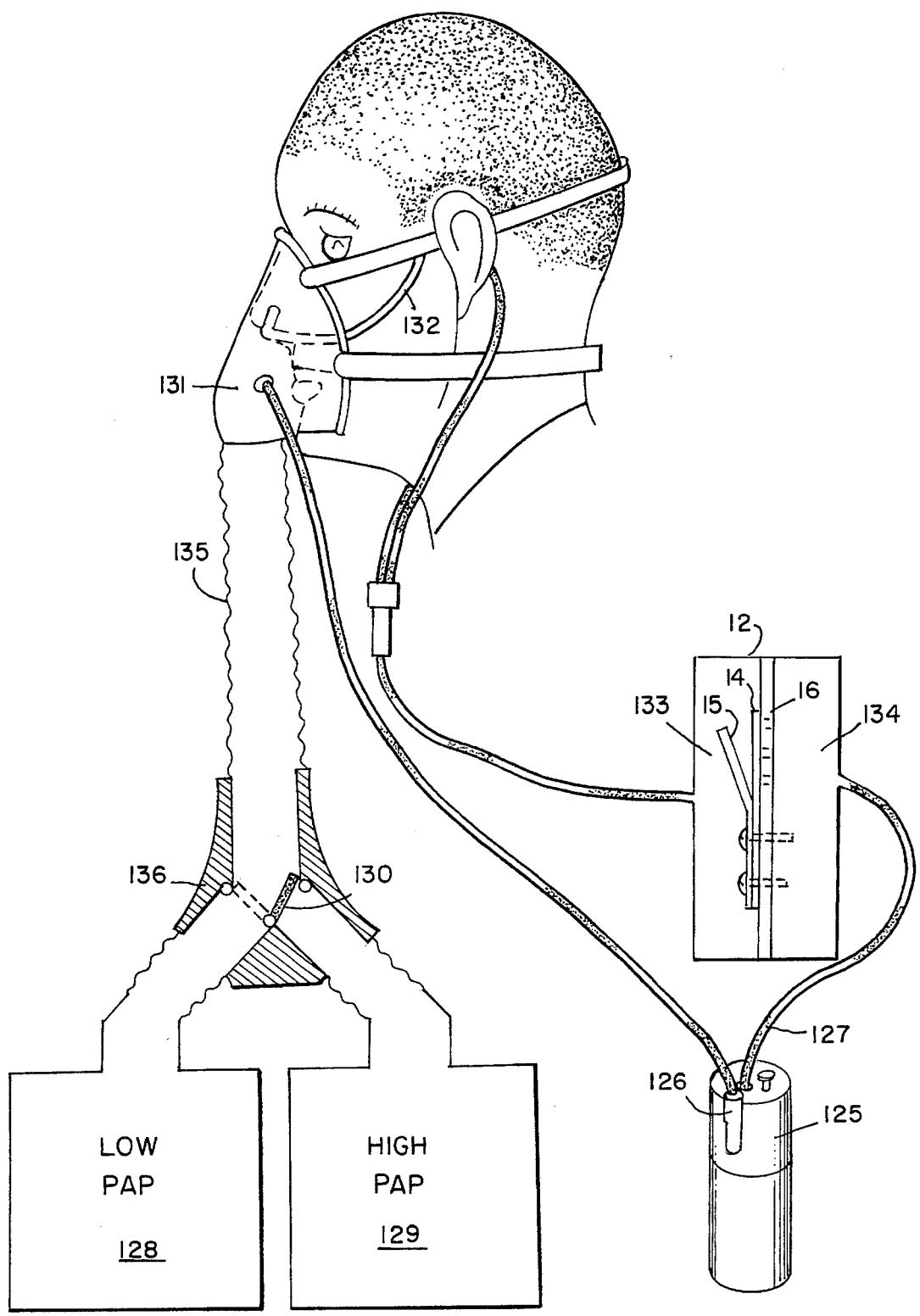
FIG. 17 is a diagrammatic view of how the monitor can be used to control ventilators employing a low positive airway pressure during exhalation which is increased to a high positive airway pressure when inhalation takes place. It also demonstrates how it can be used for applying a low and high pressure positive airway pressure as an effective therapy for sufferers of obstructive sleep apnea.

The invention can be used as a control for ventilators that employ PEEP (positive end expiratory pressure) requiring the negative inhalation pressure be sensed when there is positive air pressure being delivered during exhalation. FIG. 17 is a diagrammatic view of how the monitor can be used to control ventilators employing a low positive airway pressure during exhalation, which is increased to a high positive pressure when inhalation takes place. The patient wears nasal cannula 132, FIG. 17, which is connected to sensor 12, chamber 133 for use in detecting the negative pressure of inhalation. Mask 131, worn over the nasal cannula, covers the nose and mouth, with connection tube 135 going to valve 136 which has an electrically operated hinged vane 130 that can select one of the two sources of positive airway pressure (128, 129). A tube goes from mask 131 to connection 126 on the electrically operated solenoid valve 125; connection 127 of solenoid valve 125 is connected to chamber 134.

The theory of operation is that sensor 14, 15, and 16 acts as a differential pressure switch with its reference pressure in chamber 134 being supplied by low positive airway pressure source 128. When the devices are first turned on the pressure in chamber 133 is equal to the pressure in chamber 134 because the connection is made from mask 131 (which has the low positive airway pressure) to the electrically operated solenoid valve 125 that is open to allow the low positive airway pressure to enter chamber 134. When the patient inhales a negative pressure is present at the nasal cavities, and this results in vane 14 moving away from printed circuit board 16. As described in the preferred embodiment this results in a signal being sent to the microprocessor. This signal results in solenoid valve 125 being closed and in vane 130 of valve 136 being electrically moved to a new position, shutting off the low positive airway pressure source 128, and sending the high positive airway pressure of source 129 to mask 131 where it inflates the lung cavities. Vane 14 is then subject to the high positive airway pressure source 129, and is returned to its original position adjacent to printed circuit board 16. Pressure from the high positive airway pressure is applied for the period of inhalation as described in the preferred embodiment. At the end of the dose, valve 130 is moved to deliver only the low positive airway pressure to mask 131, and valve 125 is again open to deliver the low positive airway pressure and have chamber 134 pressure equal to pressure in chamber 133.

The method described results in the ventilator responding to the patient's breathing and contributes to overall patient synchronizing with the mechanical ventilator.

It's ability to sense the onset of inhalation and to limit inspiratory time prevents patient dyssynchrony that can create problems for patient.[5]

[5]. Kacmarek R. M.: Management of patient—mechanical ventilator system, in Pierson D, Kacmarek R. M. (eds): Foundations of Respiratory Care, New York, Churchill Livingstone 1992 PP 973–998

If the pressure sources 128 and 129 are replaced with blowers, such that source 128 is replaced with a blower output of approximately 0 to 4 inches of water gauge static pressure, and source 129 is replaced with a blower output approximately of 1 to 9 inches of water gauge static pressure, the apparatus in FIG. 17 can be used for therapeutic treatment for sufferers of obstructive sleep apnea to provide two constant positive airway pressures to the patient's nasal passages to remove the obstruction caused by the soft palate at the base of the throat, and the uvula.

While the invention has been particularly shown and described with references to the preferred embodiments thereof, it will be understood by those skilled in the art that various alterations in form and detail may be made therein without departing from the spirit and scope of the invention. Moreover, while the invention has been particularly shown and described for health care (with a human), it should be understood the invention may be used for its primary purpose of detecting low pressure (either positive, negative, or differential), and that its use of a micro-controller chip allows it to use data obtained by sensing, to have control capabilities to store programs that govern, in a predetermined manner, operation of devices for use in industry, health care, prevention of pollution, and can also be used in a subject in aeronautical, industrial, subterranean or underwater environments.

I claim:

1. An apparatus for monitoring low pressure intervals and controlling delivery of therapeutic gas to be synchronous with inhalation comprising:

a) a source of therapeutic gas;

b) means for delivering the therapeutic gas from the source to nasal cavities of an air breathing animal;

c) sensing means, connected to the means for delivering, for generating a signal indicative of a change in pressure produced at a beginning of inhalation of the air breathing animal, said sensing means including a vane;

d) processing means for receiving the signal and determining a length of inhalation of the animal, said processing means including circuit means for determining a dose of the therapeutic gas to be delivered to the animal, the circuit means including means for automatically adjusting a length of the dose to be a percentage of the length of the inhalation of the animal with the length of the dose never less than 200 mS;

e) means for controlling delivery of the dose of therapeutic gas; and f) alarm means for generating an alarm when the sensing means does not generate the signal for a predetermined time period.

2. The apparatus as set forth in claim 1, having means for controlling delivery of the dose of therapeutic gas wherein:

said means for delivering includes a valve to obtain a controllable flow; and means for reducing electrical power requirements by reducing power input to said valve immediately after said valve is actuated to obtain longer battery life.

* * * * *